United States Patent [19]

Rowsell et al.

[11]  4,230,688

[45]  * Oct. 28, 1980

[54] ACYCLIC CARBOXAMIDES HAVING A PHYSIOLOGICAL COOLING EFFECT

[75] Inventors: David G. Rowsell, Staines; David J. Spring, Datchet; Roger Hems, Maidenhead, all of England

[73] Assignee: Wilkinson Sword Limited, London, England

[*] Notice: The portion of the term of this patent subsequent to May 8, 1996, has been disclaimed.

[21] Appl. No.: 36,662

[22] Filed: May 7, 1979

Related U.S. Application Data

[60] Continuation of Ser. No. 768,219, Feb. 14, 1977, Pat. No. 4,153,679, which is a division of Ser. No. 351,357, Apr. 16, 1973, abandoned.

[30] Foreign Application Priority Data

Apr. 18, 1972 [GB] United Kingdom ............... 17914/72

[51] Int. Cl.³ .......................... A61K 7/16; A61L 9/04

[52] U.S. Cl. .................................. 424/45; 131/10 R; 131/17 R; 131/144; 132/89; 252/522 A; 424/48; 424/49; 424/73; 424/320; 424/329

[58] Field of Search ........................... 424/320, 45, 49

[56] References Cited

U.S. PATENT DOCUMENTS

| | | | |
|---|---|---|---|
| 2,166,119 | 7/1939 | Bosquet | 424/320 |
| 3,644,653 | 2/1972 | Tchelitcheff | 424/358 |

OTHER PUBLICATIONS

Chemical Abstracts 72:70581(a), 1969.

Primary Examiner—Leonard Schenkman
Attorney, Agent, or Firm—Leydig, Voit, Osann, Mayer & Holt, Ltd.

[57]  ABSTRACT

Compositions are disclosed having a physiological cooling action on the skin. The compositions contain, as the active ingredient, certain acyclic tertiary and secondary carboxamides.

15 Claims, No Drawings

ACYCLIC CARBOXAMIDES HAVING A PHYSIOLOGICAL COOLING EFFECT

This application is a continuation of U.S. application Ser. No. 768,219, 02/14/77, now U.S. Pat. No. 4,153,679, which was a division of U.S. application Ser. No. 351,357, filed on Apr. 16, 1973, now abandoned.

This invention relates to ingestible, topical and other compositions having a physiological cooling effect on the skin and on the mucous membranes of the body, particularly the mucous membranes of the nose and bronchial tract.

Menthol is well known for its physiological cooling effect on the skin and mucous membranes of the mouth and has been extensively used as a flavouring agent (menthol being a major constituent of oil of peppermint) in foodstuffs, beverages, dentifrices, mouthwashes, etc. and as a component in a wide range of toiletries, liniments and lotions for topical application. Menthol is also a well known tobacco additive for producing a "cool" sensation in the mouth when smoking. Carvomenthol has also been reported as having a physiological cooling effect and so also have N,N-dimethyl-2-ethyl butanamide and N,N-diethyl-2-ethyl butanamide, see French Pat. No. 1,572,332.

It is well established that the "cooling" effect of menthol is a physiological effect due to the direct action of menthol on the nerve endings of the human body responsible for the detection of hot or cold and is not due to latent heat of evaporation. It is believed that the menthol acts as a direct stimulus on the cold receptors at the nerve endings which in turn stimulate the central nervous system.

Although menthol is well established as a physiological coolant its use, in some compositions, is circumscribed by its strong minty odour.

The present invention is based on the discovery that certain other organic compounds, which can be readily synthesised, have a physiological cooling effect similar to that obtained with menthol, but do not have the strong minty odour. In many cases the compounds have little or no odour at all. Such compounds therefore find utility as additives in a wide range of ingestible and topical compositions. More particularly they find utility as components in compositions for nasal application and in vapour rubs and liniments.

The compounds having a physiological cooling effect and utilizable in accordance with the present invention are amides of the formula:

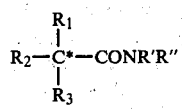

where
R' and R", when taken separately, are each hydrogen, $C_1-C_5$ alkyl or $C_1-C_8$ hydroxyalkyl and provide a total of no more than 8 carbon atoms, with the proviso that when R' is hydrogen R" may also be alkylcarboxyalkyl of up to 6 carbon atoms;
R' and R", when taken together, represent an alkylene group of up to 6 carbon atoms, the opposite ends of which group are attached to the amide nitrogen atom thereby to form a nitrogen heterocycle, the carbon atom chain of which may optionally be interrupted by oxygen;
$R_1$ is hydrogen or $C_1-C_5$ alkyl; and
$R_2$ and $R_3$ are each $C_1-C_5$ alkyl;
with the provisos that
(i) $R_1$, $R_2$ and $R_3$ together provide a total of at least 5 carbon atoms, preferably from 5–10 carbon atoms; and
(ii) when $R_1$ is hydrogen, $R_2$ is $C_2-C_5$ alkyl and $R_3$ is $C_3-C_5$ alkyl and at least one of $R_2$ and $R_3$ is branched, preferably in an alpha or beta position relative to the carbon atom marked (*) in the formula.

Where the compounds used in this invention have an asymmetric carbon atom either optical isomer may be used in pure form but generally a mixture of optical isomers will be used. In some cases the degree of cooling produced by the compounds on the skin will differ as between optical isomer, in which case one or other isomer may be preferred.

The preferred amides used in this invention are the tertiary compounds, i.e. those where each of $R_1$, $R_2$ and $R_3$ is $C_1-C_5$ alkyl, especially those where $R_1$ is methyl, ethyl or n-propyl and at least one of $R_2$ and $R_3$ is a branched chain group having branching in an alpha or beta position relative to the C atom marked (*) in the formula. Also preferred are mon-substituted amides, i.e. where R' is H, and disubstituted amides where R' and R" are methyl or ethyl. A further preferred group consists of amides of the formula given where $R_1$ is hydrogen and at least one of $R_2$ and $R_3$ is branched in an alpha position relative to the carbon atom marked * in the formula.

The amides may readily be prepared by conventional techniques, for example, by reaction of an acid chloride of the formula $R_1R_2R_3COCl$ with an amine of the formula HNR'R" in the presence of a hydrogen chloride acceptor. Such reactions are entirely conventional and the procedures involved will readily be understood by persons skilled in the art.

Typical amides usable in the compositions of this invention are listed below in the Table together with an indication of their cooling activity; the more stars the greater the activity, i.e. the greater the degree of cooling produced by a given quantity of the compound.

| $R_1$ | $R_2$ | $R_3$ | R' | R" | Activity |
|---|---|---|---|---|---|
| $CH_3-$ | iso-$C_3H_7-$ | iso-$C_3H_7$ | H— | $C_2H_5-$ | * * * * * |
| " | " | " | " | iso-$C_3H_7-$ | * * * * * |
| " | " | " | " | $CH_3-$ | * * * * * |
| " | " | " | " | $HOCH_2C(CH_3)_2-$ | * * * * * |
| " | " | " | $CH_3-$ | $CH_3-$ | * * * * * |
| $CH_3-$ | iso-$C_3H_7-$ | " | H— | tert-$C_4H_9-$ | * * * * * |
| $C_2H_5-$ | $C_2H_5-$ | " | H— | $C_2H_5-$ | * * * * * |
| " | " | " | $C_2H_5-$ | $C_2H_5-$ | * * * * * |
| $CH_3-$ | iso-$C_3H_7-$ | iso-$C_4H_9-$ | H— | $C_2H_5-$ | * * * * * |
| $C_2H_5-$ | iso-$C_3H_7-$ | iso-$C_3H_7-$ | H— | $C_2H_5-$ | * * * * * |

-continued

| R₁ | R₂ | R₃ | R' | R" | Activity |
|---|---|---|---|---|---|
| H | sec-C₄H₉— | sec-C₄H₉— | H— | sec-C₄H₉— | * * * * * |
| CH₃— | iso-C₃H₇— | n-C₄H₉— | CH₃ | CH₃ | * * * * * |
| H— | iso-C₄H₉— | sec-C₄H₉— | H— | C₂H₅— | * * * * * |
| CH₃— | sec-C₄H₉— | " | H— | " | * * * * * |
| CH₃ | iso-C₃H₇— | iso-C₃H₇— | H— | C₂H₅OOCCH₂— | * * * * |
| C₂H₅— | C₂H₅— | C₂H₅— | H— | C₂H₅— | * * * * |
| CH₃— | sec-C₄H₉— | sec-C₄H₉— | H— | iso-C₃H₇— | * * * * |
| CH₃— | iso-C₃H₇— | n-C₄H₉— | H— | C₂H₅— | * * * * |
| CH₃— | iso-C₄H₉— | iso-C₄H₉— | H— | " | * * * * |
| CH₃— | CH₃— | " | " | " | * * * * |
| " | " | " | CH₃— | CH₃— | * * * * |
| H— | iso-C₄H₉ | " | H— | C₂H₅OOCCH₂— | * * * * |
| H— | C₂H₅— | sec-C₄H₉— | CH₃— | CH₃— | * * * * |
| " | " | " | H— | C₂H₅— | * * * * |
| " | iso-C₄H₉— | " | H— | C₂H₅OOCCH₂— | * * * * |
| " | " | " | " | HOCH₂C(CH₃)₂— | * * * * |
| CH₃— | iso-C₄H₉— | iso-C₄H₉ | 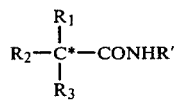 | | * * * * |
| " | iso-C₃H₇— | iso-C₃H₇— | H— | C₂H₅OOCCH₂— | * * * |
| C₂H₅— | C₂H₅— | C₂H₅— | " | HOCH₂C(CH₃)₂ | * * * |
| CH₃— | sec-C₄H₉— | sec-C₄H₉— | " | HOCH₂CH₂— | * * * |
| CH₃— | sec-C₄H₉— | " | " | H— | * * * |
| CH₃— | iso-C₄H₉— | iso-C₄H₉— | " | C₂H₅— | * * * |
| H— | iso-C₃H₇— | iso-C₄H₉— | " | " | * * * |
| H— | iso-C₄H₉— | " | " | C₂H₅OOCCH₂— | * * * |
| H— | iso-C₃H₇— | " | " | " | * * |
| H— | C₂H₅— | iso-C₃H₇— | CH₃— | CH₃— | * * |
| H— | iso-C₄H₉— | iso-C₄H₉— | H— | HOCH₂C(CH₃)₂— | * * |
| H— | C₂H₅— | iso-C₅H₁₁— | " | C₂H₅— | * * |
| CH₃— | iso-C₃H₇— | iso-C₄H₉— | O⟨CH₂-CH₂ / CH₂-CH₂⟩ | | * * |
| H | " | iso-C₃H₇— | H— | iso-C₃H₇ | * * |
| C₂H₅— | C₂H₅— | C₂H₅— | CH₃— | CH₃— | * |
| CH₃— | " | " | " | " | * |
| " | " | " | H— | C₂H₅OOCCH₂— | * |
| " | CH₃— | iso-C₄H₉— | " | " | * |
| H— | " | " | " | HOCH₂C(CH₃)₂— | * |
| H— | C₂H₅— | sec-C₄H₉— | " | " | * |
| CH₃— | iso-C₃H₇— | iso-C₃H₇— | " | H— | * |
| C₂H₅— | C₂H₅— | iso-C₃H₇— | " | " | * |

Certain amides used in the present invention and preparable by the above described method are novel compounds and as such represent a further aspect of the present invention. The novel compounds are monosubstituted tertiary amides of the formula:

$$R_2-\overset{R_1}{\underset{R_3}{C^*}}-CONHR'$$

where $R_1$, $R_2$ and $R_3$ are each $C_1$-$C_5$ alkyl and together provide a total of at least 5, preferably 5–10 carbon atoms; and R' is $C_1$-$C_5$ alkyl, $C_1$-$C_8$ hydroxyalkyl or alkylcarboxyalkyl of up to 8 carbon atoms. In this group $R_1$ is preferably methyl, ethyl or n-propyl and one or both of $R_2$ and $R_3$ is branched in an alpha or beta position relative to the carbon atom marked (*).

The compounds of the above formulae find utility in a wide variety of compositions for consumption by or application to the human body. Broadly speaking, these compositions can be divided into comestible and topical compositions, both terms being taken in their broadest possible sense. Thus comestible is to be taken as including not only foodstuffs and beverages taken into the mouth and swallowed, but also other orally ingested compositions taken for reasons other than their nutritional value, e.g. indigestion tablets, antacid preparations, laxatives etc. Comestible compositions are also to be taken to include edible compositions taken by mouth, but not necessarily swallowed, e.g. chewing gum. Topical compositions are to be taken as including not only compositions such as perfumes, powders and other toiletries, lotions, liniments, oils and ointments applied to the external surfaces of the human body, whether for medical or other reasons, but also compositions applied to, or which, in normal usage, come in contact with, internal mucous membranes of the body, such as those of the nose, mouth, or throat, whether by direct or indirect application or inhalation, and thus include nasal and throat sprays, dentifrice, mouthwash and gargle compositions. Also included within the present invention are toilet articles such as cleansing tissues and toothpicks impregnated or coated with the active cooling compound.

A further class of compositions included within the scope of this invention are tobacco and associated articles e.g. pipe and cigarette filters, especially filter tips for cigarettes.

The compositions of this invention will contain an amount of the active cooling compound sufficient to stimulate the cold receptors in the areas of the skin or mucous membrane with which the compositions come into contact and thereby promote the desired cold sensation. As the degree and longevity of cooling sensation varies from compound to compound the quantity of stimulant used in each composition will vary widely. As a guide, it may be said that, with the more active compounds, a significant cooling sensation, which, in some cases, may persist for several hours, is achieved upon application to the skin of as little as 0.05 ml. of a 1.0% weight percent solution of the active ingredient in ethanol. For the less active compounds a significant cooling effect is achieved only with more concentrated solutions, e.g. 5.0% by weight or more of the active ingredient. It must also be admitted that such skin tests are somewhat subjective, some individuals experiencing a greater or lesser cooling sensation than others when subjected to the same test.

In formulating the compositions of this invention the active cooling compound will usually be incorporated into a carrier which may be completely inert or which may be or contain other active ingredients. A wide variety of carriers will be suitable, depending upon the end use of the composition, such carriers including solids, liquids, emulsions, foams and gels. Typical carriers for the active cooling compound include aqueous or alcoholic solutions; oils and fats such as hydrocarbon oils, fatty acid esters, long chain alcohols and silicone oils; finely divided solids such as starch or talc; cellulosic materials such as paper tissue; tobacco; low-boiling hydrocarbons and halohydrocarbons used as aerosol propellants; gums and natural or synthetic resins.

In most compositions according to the invention the carrier will be or contain as an adjuvant one or more of the following: an antacid, antiseptic or analgesic, a flavourant, colourant, or odourant, or a surfactant.

The following illustrate the range of compositions into which the active cooling compounds can be incorporated:

1. Edible or potable compositions including alcoholic and non-alcoholic beverages, confectionery, chewing gum; cachous; ice cream; jellies;
2. Toiletries including after shave lotions, shaving soaps, creams and foams, toilet water, deodorants and antiperspirants, "solid colognes," toilet soaps, bath oils and salts, shampoos, hair oils, talcum powders, face creams, hand creams, sunburn lotions, cleansing tissues, dentifrices, toothpicks, mouthwashes, hair tonics, eyedrops.
3. Medicaments including antiseptic ointments, pile ointments, liniments, lotions, decongestants, counter-irritants, cough mixtures, throat lozenges, antacid and indigestion preparations, oral analgesics;
4. Tobacco preparations including cigars, cigarettes, pipe tobacco, chewing tobacco and snuff; tobacco filters, especially filter tips for cigarettes.
5. Miscellaneous compositions such as water soluble adhesive compositions for envelopes, postage stamps, adhesive labels etc.

Particular preparations according to the invention are discussed in more detail below.

Edible and Potable Compositions

The edible and potable compositions of this invention will contain the active cooling compound in combination with an edible carrier and usually a flavouring or colouring agent. The particular effect of the cooling compounds is to create a cool or fresh sensation in the mouth, and in some cases, even in the stomach, and therefore the compounds find particular utility in sugar-based confectionery such as chocolate, boiled sweets and candy, in ice cream and jellies and in chewing gum. The formulation of such confections will be by ordinary techniques and according to conventional recipes and as such forms no part of this invention. The active compound will be added to the recipe at a convenient point and in amount sufficient to produce the desired cooling effect in the final product. As already indicated, the amount will vary depending upon the particular compound, the degree of cooling effect desired and the strength of other flavourants in the recipe. For general guidance, however, amounts in the range 0.1 to 5% by weight based on the total composition will be found suitable.

Similar considerations apply to the formulation of beverages. Generally speaking the compounds will find most utility in soft drinks e.g. fruit squashes, lemonade, cola etc., but may also be used in alcoholic beverages. The amount of compound used will generally be in the range 0.1 to 2.5% by weight based on the total composition.

Toiletries

Because of the cooling sensation imparted to the skin, a major utility of the cooling compounds will be in a wide range of toilet preparations and toilet articles. The particular preparations discussed below are to be taken as exemplary.

A major utility will be in after shave lotions, toilet water etc., where the compound will be used in alcoholic or aqueous alcoholic solution, such solutions usually also containing a perfume or mild antiseptic or both. The amount of compound added to the formulation will usuallly be in the range 0.1 to 10% by weight based on the total composition.

Another field of utility will be in soaps, shampoos, bath oils etc. where the compound will be used in combination with an oil or fat or a natural or synthetic surfactant e.g. a fatty acid salt or a lauroylsulphate salt, the composition usually also containing an essential oil or perfume. The range of soap compositions will include soaps of all kinds e.g. toilet soaps, shaving soaps, shaving foams etc. Usually the compound will be added to the formulation in amount of from 0.1 to 10% by weight.

A further class of toilet compositions into which the compounds may be incorporated includes cosmetic creams and emollients, such creams and emollients usually comprising a base emulsion and optionally a range of ingredients such as wax, preservative, perfume, antiseptics, astringents, pigments etc. Also included within this class are lipstick compositions such compositions usually comprising an oil and wax base into which the compound can be incorporated along with the conventional ingredients, i.e. pigments, perfumes etc. Once again the formulation of such compositions, apart from the incorporation of the cooling compound, usually in an amount of from 0.05 to 10% by weight, is conventional.

Compositions for oral hygiene containing the cooling compounds include mouthwash, gargle and dentifrice compositions. The first two may be considered together and will usually comprise an aqueous, alcoholic, or aqueous-alcoholic solution of an antiseptic often coloured or flavoured for palatability, to which the coolant is added in an amount of from 0.1 to 1.0% by weight.

Dentifrice compositions may be of the solid block, powder, paste or liquid type and will usually comprise a finely divided abrasive or polishing material, e.g. precipitated chalk, silica, magnesium silicate, aluminium hydroxide or other similar materials well known in the art, and a detergent or foaming agent. Optional ingredients which may also be included are flavouring agents and colourants, antiseptics, lubricants, thickeners, emulsifiers or plasticizers. The amount of coolant added in such compositions will generally be from 0.1 to 5.0% by weight based on the total composition.

Medicaments

Because of their cooling effect on the skin and on the mucous membranes of the mouth, throat and nose and of the gastrointestinal tract the cooling compounds may be used in a variety of oral medicines, nasal and throat sprays, and topical compositions, particularly where a counter-irritant is required. In particular the coolants may be formulated into antacid and indigestion remedies, in particular those based on sodium bicarbonate, magnesium oxide, calcium or magnesium carbonate, aluminium or magnesium hydroxide or magnesium trisilicate. In such compositions the coolant will usually be added in an amount of from 0.01 to 2.0% by weight.

The coolants may also be included in oral analgesic compositions e.g. with acetylsalicylic acid or its salts, and in nasal decongestants e.g. those containing ephedrine.

Tobacco Preparations

The coolants of this invention may be incorporated directly into tobacco to give a cool effect when smoking but without the attendant strong and characteristic odour which is associated with mentholated tobacco and cigarettes. However, a more advantageous utilisation of the coolants of this invention is in pipe or cigarette filters, in particular, filter tipped cigarettes. The pad of filter material, which may be of any of the well known types, e.g. cellulose acetate, paper, cotton α-cellulose or asbestos fiber, is simply impregnated with an alcoholic solution of the coolant and dried to deposit the coolant in the filter pad. The effect is to give a pleasant cool sensation in the mouth when the cigarette is smoked. As little as 0.1 mg. of the coolant is effective.

Compositions of this invention are illustrated by the following Examples.

EXAMPLE I

After Shave Lotion

An after shave lotion was prepared according to the following recipe by dissolution of the ingredients in the liquid and cooling and filtering:
Denatured Ethanol: 75%
Diethylphthalate: 1.0%
Propylene Glycol: 1.0%
Lactic Acid: 1.0%
Perfume: 3.0%
Water: to 100%

Into the base lotion was added 0.5% by weight based on the total composition of N,2,3-trimethyl-2-isopropylbutanamide. When the final lotion is applied to the face a clearly noticeable cooling effect becomes apparent after a short interval of time.

EXAMPLE II

Eye Lotion

An eye lotion was prepared containing the following ingredients:

Witch Hazel: 12.95%
Boric Acid: 2.00%
Sodium Borate: 0.50%
Allantoin: 0.05%
Salicylic Acid: 0.025%
Chlorobutol: 0.02%
Zinc Sulphate: 0.004%
Water: to 100%

To the formulation was added 0.01%, based on the total composition of N-(2-isopropyl-2,3-dimethylbutanoyl)glycine ethyl ester. When used to bathe the eyes a cool fresh sensation is apparent on the eyeball and eyelids.

EXAMPLE III

Toothpaste

The following ingredients were mixed in a blender:
Dicalcium phosphate: 48.0%
Sodium lauryl sulphate: 2.5%
Glycerol: 24.8%
Sodium carboxymethyl cellulose: 2.0%
Citrus flavourant: 1.0%
Sodium saccharin: 0.5%
Water: to 100%

Shortly before completion of the blending operation 1.0% by weight N,N,2,3-tetramethyl-2-isopropylbutanamide was added to the blender. When applied as a toothpaste, a cooling effect is noticed in the mouth.

EXAMPLE IV

Soft Sweet

Water was added to icing sugar at 40% to form a stiff paste. 0.5% of N-ethyl 2,2-diisopropylbutanamide was then stirred into the paste and the mixture allowed to set. A soft sweet mass resulted having the characteristic cooling effect in the mouth of peppermint but without the minty flavour or odour.

EXAMPLE V

Cigarette Tobacco

A proprietary brand of cigarette tobacco was impregnated with an alcoholic solution of N-ethyl 2-isopropyl-2,3-dimethylbutanamide, dried and rolled into cigarettes each containing approximately 0.00025 gm. of active compound. Smoking the impregnated cigarettes produced a cool effect in the mouth characteristic of mentholated cigarettes.

A similar effect is noticed when smoking a proprietary brand of tipped cigarette, the coolant being used to impregnate the filter tip rather than the tobacco.

EXAMPLE VI

Antiseptic Ointment

An ointment was prepared according to the following formulation:
Cetyltrimethyl ammonium bromide: 4.0%
Cetyl Alcohol: 6.0%
Stearyl Alcohol: 6.0%
White Paraffin: 14.0%
Mineral Oil: 21.0%
Water: to 100%

The ingredients were mixed, warmed to 40° C. and emulsified in a high speed blender. Added to the mixture during blending was 1.5% of N,N,2-trimethyl-2-isopropylhexanamide.

The final ointment when applied to the skin gave rise to a marked cooling effect.

EXAMPLE VII

Aerosol Shaving Soap

An aerosol shaving soap composition was formulated according to the following recipe:
Stearic acid: 6.3%
Lauric acid: 2.7%
Triethanolamine: 4.6%
Sodium carboxymethyl cellulose: 0.1%
Sorbitol: 5.0%
Perfume: 0.4%
Water: to 100%

The composition was prepared by fusing the acids in water, adding the triethanolamine, cooling and adding the other constituents. To the mixture was then added 0.5% based on the total composition of N,2,2-triethyl-3-methylbutanamide. The composition was then packaged in an aerosol dispenser under pressure of a butane propellent.

When used in shaving a fresh cool sensation was distinctly noticeable on the face.

EXAMPLE VIII

Toilet Water

A toilet water was prepared according to the following recipe:
Denatured ethanol: 75.0%
Perfume: 5.0%
Water: to 100%

To the recipe was added 2.0%, based on the total composition, of N-ethyl 2-sec-butyl-2,3-dimethylpentanamide.

As with the after shave lotion, a cooling effect was clearly noticeable on the skin well after the termination of any cooling effect attributable to the evaporation of the alcoholic carrier.

EXAMPLE IX

Deodorant Composition

A deodorant composition suitable for formulation and dispensing as an aerosol under pressure of a suitable propellent was formulated according to the following recipe:
Denatured ethanol: 96.9%
Hexachlorophene: 2.0%
Isopropyl myristate: 1.0%
Perfume: 0.1%

To the composition was added 2% by weight of N,N,2,2-tetraethyl-3-methylbutanamide. Application of the final composition gave rise to a definite cooling sensation on the skin.

EXAMPLE X

Hair Shampoo

Sodium lauryl ether sulphate, 10 g., was dispersed in 90 g. water in a high speed mill. To the dispersion was added 2% by weight of N-(1,1-dimethyl-2-hydroxyethyl)-2-isopropyl-2,3-dimethylbutanamide. When the hair is washed using the shampoo a fresh, cool sensation is noticed on the scalp.

EXAMPLE XI

Solid Cologne

A solid cologne was formulated according to the following recipe:
Denatured ethanol: 74.5%
Propylene glycol: 3.0%
Sodium stearate: 5.0%
Perfume: 5.0%
Water: to 100%

The sodium stearate was dissolved by stirring in a warm mixture of the ethanol, propylene glycol and water. To the solution was added the perfume and 2% of N,N,2-dimethyl-2-isopropylhexanamide and the mixture then allowed to solidify into a waxy cake.

When applied to the forehead a distinct cooling effect is noticeable.

EXAMPLE XII

Mouthwash

A concentrated mouthwash composition was prepared according to the following recipe:
Ethanol: 3.0%
Borax: 2.0%
Sodium bicarbonate: 1.0%
Glycerol: 10.0%
Flavourant: 0.4%
Thymol: 0.03%
Water: to 100%

To the composition was added 0.1% of N-(1,1-dimethyl-2-hydroxyethyl)-2,2-diethylbutanamide.

When diluted with approximately 10 times its own volume of water and used to rinse the mouth a cooling effect is obtained in the mouth.

EXAMPLE XIII

Toothpicks

The tip of a wooden toothpick was impregnated with an alcoholic solution containing N-ethyl 2,2-diisopropylbutanamide in sufficient amount to deposit on the toothpick 0.05 mg. of the compound. The impregnated toothpick was then dried. When placed on the tongue there is no detectable taste, however, a distinct cooling effect is noticeable after a short period of time.

EXAMPLE XIV

Soft Drink

A soft drink concentrate was prepared from the following recipe:
Pure orange juice: 60%
Sucrose: 10%
Saccharin: 0.2%
Orange flavouring: 0.1%
Citric acid: 0.2%
Sulphur dioxide: trace amount
Water: to 100%

To the concentrate was added 0.10% of N,2,3-trimethyl-2-isopropylbutanamide.

The concentrate was diluted with water and tested. An orange flavour having a pleasantly cool after-effect was obtained.

EXAMPLE XV

Boiled Sweet 99.5% sucrose and 0.5% citric acid were carefully fused together in the presence of a trace of water. Just before casting the melt onto a chilled plate 0.5% of N-ethyl 2-methyl-2-isopropylhexanamide was rapidly stirred in.

The melt was then cast. A boiled sweet resulted having a marked cooling effect on the mouth.

EXAMPLE XVI

Indigestion tablet

The following ingredients were ground together:
Magnesium carbonate: 49.5%
Sorbitol: 49.4%
Saccharin: 0.1%
Talc: 1.0%

Added to the mixture during grinding was 0.10% of N-ethyl 2-isobutyl-2,4-dimethylpentanamide. After mixing the mixture was pressed into 0.5 g tablets.

Taken by mouth and swallowed the tablets produced after a short interval of time a noticeable cooling effect in the stomach.

EXAMPLE XVII

Cleaning Tissue

A cleansing tissue was prepared having the formulation:
Triethanolamine Lauryl sulphate: 1.0%
Glycerol: 2.0%
Perfume: 0.95%
Water: to 100%

To this liquid was added 1.0% of N-ethyl 2-isopropyl-2,3-dimethylbutanamide. A paper tissue was then soaked in the liquid.

When the impregnated tissue was used to wipe the skin a fresh cool sensation developed on the skin after a short interval.

The above Examples illustrate the range of compounds and the range of compositions included within the present invention. However, they are not to be taken as limiting the scope of the invention in any way. Other compounds within the general formula will be equally suitable for use in the composition of Examples I-XVII and the physiological cooling effect obtained with the compounds of the invention will recommend their use in a wide variety of other compositions where the cooling effect will be of value.

The following Examples illustrate the preparation of the novel compounds of this invention. All temperatures are in degrees centigrade. The tertiary carboxylic acid starting materials were obtained by alkylation of nitriles by known techniques followed by hydrolysis.

EXAMPLE XVIII

PREPARATION OF N-ETHYL-2,3-DIMETHYL-2-ISOPROPYL-BUTANAMIDE 2,3-Dimethyl-2-isopropylbutanoic acid (22 g) was heated under reflux with thionyl chloride (50 ml) for 60 minutes. The excess of thionyl chloride was removed under reduced pressure and the 2,3-dimethyl-2-isopropylbutanoyl chloride was distilled, bp. 73°-5°/15 mm.

A portion (2 g) of the acid chloride in ether (20 ml) was added dropwise to a stirred solution of ethylamine (5 ml of a 70% solution in water) in ether (100 ml.). The mixture was stirred for 1 hour. The ether layer was then washed with water, dilute hydrochloric acid and water. The dried (MgSO$_4$) ether solution was concentrated, and the residue distilled to give N-ethyl-2,3-dimethyl-2-isopropylbutanamide, bp. 93°-5°/1.5 mm, as a colourless liquid which rapidly solidified to a colourless solid mp. 38°-40°.

EXAMPLE XIX

PREPARATION of N,2,3-TRIMETHYL-2-ISOPROPYLBUTANAMIDE

The procedure of Example XVIII was repeated using methylamine in place of ethylamine. N,2,3-Trimethyl-2-isopropylbutanamide was obtained as a colourless solid, mp 58°-61°, bp. 83°-5°/0.35 mm.

EXAMPLE XX

PREPARATION OF N-(2,3-DIMETHYL-2-ISOPROPYLBUTANOYL)-GLYCINE ETHYL ESTER

Sodium bicarbonate (1.7 g, 0.02 mole) and glycine ethyl ester hydrochloride (1.4 g, 0.01 mole) were dissolved in water (10 ml) and a solution of 2,3-dimethyl-2-isopropylbutanoyl chloride (1.6 g, 0.009 mole) in ether (10 ml) was added. The mixture was stirred vigorously at room temperature for 2 hours. After 16 hours at room temperature the ether layer was separated and dried (MgSO$_4$). Removal of the solvent left a white solid which was recrystallized from ether/petroleum ether to give N-(2,3-dimethyl-2-isopropylbutanoyl)glycine ethyl ester, mp. 74.5°-75.5°.

Analysis: Found C: 64.0; H: 10.3; N: 5.9. Calculated C: 64.2; H: 10.3; N: 5.8%.

EXAMPLE XXI

PREPARATION OF N-(1,1-DIMETHYL-2-HYDROXYETHYL)-2,2-DIETHYLBUTANAMIDE 2,2-Diethylbutanoyl chloride was prepared from 2,2-diethylbutanoic acid and thionyl chloride in the usual way.

A solution of this acid chloride (1.2 g) in ether (30 ml) was added to a stirred solution of 2-amino-2-methylpropan-1-ol (4.0 g) in ether (90 ml). After 4 hours the ethereal solution was washed with dilute hydrochloric acid and water, dried (MgSO$_4$), and concentrated. The residue was distilled to give N-(1,1-dimethyl-2-hydroxyethyl)-2,2-diethylbutanamide, bp. 113°-5°/0.9 mm, mp. 57°-8°.

Analysis: Found C: 67.5; H: 12.0; N: 6.6. Calculated C: 67.0; H: 11.6; N: 6.5.

EXAMPLE XXII

PREPARATION OF N-ETHYL-2-ISOBUTYL-2,4-DIMETHYLPENTANAMIDE 2-isobutyl-2,4-dimethylpentanoyl chloride (bp. 97°-100°/16 mm) was prepared in the usual way from 2-isobutyl-2,4-dimethylpentanoic acid (prepared by the alkylation of ethyl cyanide with 2 equivalents of isobutyl bromide, followed by hydrolysis) and thionyl chloride. A solution of the acid chloride (1.5 g) in ether (20 ml) was added with stirring to a solution of ethylamine (5 ml of a 70% solution in water) in ether (100 ml). After stirring for 2 hours the ethereal layer was washed with dilute hydrochloric acid and water. The dried (MgSO$_4$) ether solution was concentrated and the residue was recrystallized from petroleum ether (bp. 40°-60°) to give N-ethyl-2-isobutyl-2,4-dimethylpentanamide, mp. 71.5°-72.5°.

Analysis: Found C: 72.9; H: 12.3; N: 6.9. Calculated C: 73.3; H: 12.8; N: 6.6%.

EXAMPLE XXIII

PREPARATION OF N-ISOPROPYL-2-SEC-BUTYL-2,3-DIMETHYL-PENTANAMIDE 2-sec-butyl-2,3-dimethylpentanoyl chloride (bp. 108°–110°/17 mm) was prepared in the usual way from 2-sec-butyl-2,3-dimethylpentanoic acid and thionyl chloride. A solution of this acid chloride (2.0 g) in ether (30 ml) was added with stirring to a solution of isopropylamine (2.0 g) in ether (100 ml). After 16 hours the ethereal solution was washed with dilute hydrochloric acid and water, dried (MgSO$_4$), and concentrated to give a white solid. This solid was recrystallized from petroleum ether (bp. 40°–60°) to give N-isopropyl-2-sec-butyl-2,3-dimethylpentanamide, MP. 74°–6°.

Analysis: Found C: 74.3; H: 13.1; N: 6.2. Calculated C: 74.0; H: 12.8; N: 6.2%.

EXAMPLE XXIV

PREPARATION OF N-(2-HYDROXYETHYL)-2-SEC-BUTYL-2,3-DIMETHYLPENTANAMIDE

A solution of 2-sec-butyl-2,3-dimethylpentanoyl chloride (2.0 g) in benzene (10 ml) was added to a stirred solution of ethanolamine (2.0 g) in benzene (100 ml). After 16 hours the benzene solution was washed with dilute hydrochloric acid and water, dried (MgSO$_4$) and concentrated to give a pale yellow syrup. Distillation of this syrup gave N-(2-hydroxyethyl)-2-sec-butyl-2,3-dimethylpentanamide bp. 125°–130°/0.03 mm which slowly solidified on standing.

Analysis: Found C: 68.6; H: 11.6; N: 6.3. Calculated C: 68.2; H: 11.8; N: 6.1%.

EXAMPLE XXV

After Shave Lotion

An after shave lotion was prepared according to the following recipe by dissolution of the ingredients in the liquid and cooling and filtering:

Denatured Ethanol: 75%
Diethylphthalate: 1.0%
Propylene Glycol: 1.0%
Lactic Acid: 1.0%
Perfume: 3.0%
Water: to 100%

Into the base lotion was added 0.5% by weight based on the total composition of N,2-di-sec.butyl-3-methylpentanamide. When the final lotion is applied to the face a clearly noticeable cooling effect becomes apparent after a short interval of time.

EXAMPLE XXVI

Aerosol Shaving Soap

An aerosol shaving soap composition was formulated according to the following recipe:

Stearic acid: 6.3%
Lauric acid: 2.7%
Triethanolamine: 4.6%
Sodium carboxymethyl cellulose: 0.1%
Sorbitol: 5.0%
Perfume: 0.4%
Water: to 100%

The composition was prepared by fusing the acids in water, adding the triethanolamine, cooling and adding the other constituents. To the mixture was then added 0.5% based on the total composition of N-ethyl-2-sec.-butyl-4-methylpentanamide. The composition was then packaged in an aerosol dispenser under pressure of a butane propellant.

When used in shaving a fresh cool sensation was distinctly noticeable on the face.

The above Examples illustrate the range of compounds and the range of compositions included within the present invention. However, they are not to be taken as limiting the scope of the invention in any way.

Other compounds within the general formula will be equally suitable for use in the compositions of Examples I–XVII, XXV and XXVI and the physiological cooling effect obtained with the compounds of the invention will recommend their use in a wide variety of other compositions where the cooling effect will be of value.

We claim:

1. In a manufactured consumer product for application to or consumption by the human body, said product comprising a vehicle topically administrable to or consumable by the human body and containing as an adjuvant in said vehicle, a compound capable of stimulating the cold receptors of the nervous system in the surface tissues of the body when brought into contact therewith by topical application or consumption of the said vehicle, said product being:
   (i) A toiletry comprising a topically administrable vehicle containing as adjuvants therein (a) said cold receptor stimulating compound and (b) at least one of the following: an odourant, antiseptic, colourant or surfactant;
   (ii) a foodstuff or beverage comprising an orally ingestible vehicle containing as adjuvants therein (a) said cold receptor stimulating compound and (b) a flavourant; or
   (iii) a tobacco or tobacco-containing manufacture containing said cold receptor stimulating compound; the improvement which comprises using as said cold receptor stimulating compound an effective amount of a cold receptor stimulating acyclic carboxamide of the formula:

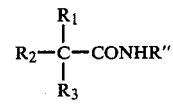

wherein
R" is C$_1$–C$_5$ alkyl, C$_1$–C$_8$ hydroxyalkyl or alkylcarboxyalkyl of up to 6 carbon atoms;
R$_1$ is H or C$_1$–C$_5$ alkyl; and
R$_2$ and R$_3$ are each C$_1$–C$_5$ alkyl;
with the provisos that
   (i) R$_1$, R$_2$ and R$_3$ together provide a total of at least 5 carbon atoms; and
   (ii) when R$_1$ is hydrogen then R$_2$ is C$_2$–C$_5$ alkyl and R$_3$ is C$_3$–C$_5$ alkyl branched at the carbon atom in the alpha or beta position.

2. A product according to claim 1, wherein R$_1$, R$_2$ and R$_3$ are each C$_1$–C$_5$ alkyl.

3. A product according to claim 1, wherein R$_1$ is methyl, ethyl or n-propyl, and at least one of R$_2$ and R$_3$ has at least three carbon atoms and is branched at the alpha or beta carbon atom.

4. A product according to claim 1, wherein R$_1$, R$_2$ and R$_3$ provide a total of from 5–10 carbon atoms.

5. A product according to claim 1, which is a toilet or cosmetic lotion comprising an aqueous, alcoholic or aqueous alcoholic carrier, an antiseptic or odorant, and an effective amount of said cold receptor stimulating compound.

6. A product according to claim 1, which is a toilet or cosmetic lotion or cream comprising an oleaginous carrier, an antiseptic or odorant, and an effective amount of said cold receptor stimulating compound.

7. A product according to claim 1, which is a shaving foam preparation comprising a foamable base, a surfactant, an odorant, or antiseptic, and an effective amount of said cold receptor stimulating compound.

8. A product according to claim 1, which is a dentifrice comprising an effective amount of said cold receptor stimulating compound.

9. A product according to claim 1, which is a mouthwash comprising an aqueous or aqueous-alcoholic carrier, an antiseptic, and an effective amount of said cold receptor stimulating compound.

10. In a foodstuff or beverage for human consumption comprising an edible or potable carrier and, as adjuvants therein, a flavorant and a compound capable of stimulating the cold receptors of the nervous system in the surface tissues of the mouth upon ingestion of the said foodstuff or beverage, the improvement which comprises using as said cold receptor stimulating compound an effective amount of a cold receptor stimulating acyclic carboxamide of the formula defined in claim 1.

11. In a chewing gum, comprising an edible chewing gum base, a flavorant and a compound capable of stimulating the cold receptors of the nervous system in the surface tissues of the mouth upon chewing said gum the improvement which comprises using as said cold receptor stimulating acyclic carboxamide of the formula defined in claim 1.

12. In a tobacco or tobacco-containing preparation comprising tobacco and a compound capable of stimulating the cold receptors of the nervous system in the surface tissues of the nose or mouth when said tobacco is ingested, or the smoke therefrom is inhaled, the improvement which comprises using as said cold receptor stimulating compound an effective amount of a cold receptor stimulating acyclic carboxamide of the formula defined in claim 1.

13. A tobacco preparation according to claim 1, which is a cigarette containing an effective amount of said cold receptor stimulating compound.

14. A tobacco preparation according to claim 1, which is a filter tip containing an effective amount of said cold receptor stimulating compound impregnated in the filter tip.

15. A method of stimulating the cold receptors of the nervous system in the surface tissues of the human body which comprises contacting said receptors with an effective amount of a cold receptor stimulating acyclic carboxamide of the formula:

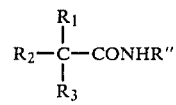

wherein
- $R''$ is $C_1-C_5$ alkyl, $C_1-C_8$ hydroxyalkyl or alkylcarboxyalkyl of up to 6 carbon atoms;
- $R_1$ is H or $C_1-C_5$ alkyl; and
- $R_2$ and $R_3$ are each $C_1-C_5$ alkyl;

with the provisos that
(i) $R_1$, $R_2$ and $R_3$ together provide a total of at least 5 carbon atoms; and
(ii) when $R_1$ is hydrogen then $R_2$ is $C_2-C_5$ alkyl and $R_3$ is $C_3-C_5$ alkyl branched at the carbon atom in the alpha or beta position.

* * * * *

UNITED STATES PATENT AND TRADEMARK OFFICE
CERTIFICATE OF CORRECTION

PATENT NO. : 4,230,688
DATED : October 28, 1980
INVENTOR(S) : David G. Rowsell et al.

It is certified that error appears in the above—identified patent and that said Letters Patent is hereby corrected as shown below:

Column 2, line 33, "$C_1-c_5$" should read --$C_1-C_5$--

Column 14, line 36 through line 41,

> "(iii) a tobacco or tobacco-containing manufacture containing said cold receptor stimulating compound; the improvement which comprises using as said cold receptor stimulating compound an effective amount of a cold receptor stimulating acyclic carboxamide of the formula:"

should read

> --(iii) a tobacco or tobacco-containing manufacture containing said cold receptor stimulating compound;

the improvement which comprises using as said cold receptor stimulating compound an effective amount of a cold receptor stimulating acyclic carboxamide of the formula:--.

Signed and Sealed this

Seventeenth Day of March 1981

[SEAL]

Attest:

RENE D. TEGTMEYER

Attesting Officer    Acting Commissioner of Patents and Trademarks